United States Patent [19]

Dickerson

[11] Patent Number: 5,609,667
[45] Date of Patent: Mar. 11, 1997

[54] PROCESS AND MATERIAL FOR BIOREMEDIATION OF HYDROCARBON CONTAMINATED SOILS

[75] Inventor: Theodore Dickerson, Jackson, Miss.

[73] Assignee: Product Services Co., Ridgeland, Miss.

[21] Appl. No.: 545,089

[22] Filed: Oct. 19, 1995

Related U.S. Application Data

[63] Continuation-in-part of Ser. No. 219,843, Mar. 30, 1994, abandoned.

[51] Int. Cl.$^6$ .................................................... C05F 11/08
[52] U.S. Cl. ............................ 71/6; 71/903; 71/904; 435/262
[58] Field of Search ................... 435/262; 71/6, 71/903, 907; 405/263, 264; 210/690, 691

[56] References Cited

U.S. PATENT DOCUMENTS

| | | | |
|---|---|---|---|
| 3,870,599 | 3/1975 | Azarowicz | 435/281 |
| 5,100,455 | 3/1992 | Pinckard et al. | 71/9 |
| 5,266,096 | 11/1993 | Slavensky | 71/6 |

*Primary Examiner*—Ferris Lander
*Attorney, Agent, or Firm*—Breiner & Breiner

[57] ABSTRACT

A powdered cellulose, containing essentially 3–8% of ammonium sulfate forms a biologically active media which preferentially adsorbs hydrocarbons in the presence of water and supports the growth of naturally occurring hydrocarbon reducing bacterial forms resulting in rapid decomposition of the adsorbed hydrocarbons into water, carbon dioxide and other benign waste products.

33 Claims, No Drawings

PROCESS AND MATERIAL FOR BIOREMEDIATION OF HYDROCARBON CONTAMINATED SOILS

RELATED APPLICATION

The present application is a continuation-in-part of Ser. No. 08/219,843 filed Mar. 30, 1994 entitled "Process and Material For Bioremediation of Hydrocarbon Contaminated Soils" and now abandoned.

BACKGROUND OF THE INVENTION

This invention relates to the field of materials and processes for the absorption and removal of hydrocarbon contaminants from ground surfaces, water or the soil.

Hydrocarbons, especially oil, refined gasoline and the like, are intensely poisonous chemicals to most plant life, and, as a result, relatively low levels of hydrocarbon contamination are capable of sterilizing soil. Therefore, the extraction and removal of hydrocarbon contaminants and spills from the ground and from ground water in the soil has become a particularly important environmental objective.

Two basic products and processes exist for the alleviation of hydrocarbon or oil spills. The first are those products and processes which are used to absorb oil from ground spills. The most noted of these are the clay absorbents formed of various forms of calcined clay and/or zeolite mixtures sold as products under such trade names as "Speedi-Dri" and other similar names. Such products are also sold widely in the form of animal litters. All such products are generally characterized in that they are particulates with physical adsorption properties that are adapted to absorb and bind hydrocarbons in a disposable form. However, an absorbent becomes contaminated in turn by the hydrocarbon and, thus, still presents a major disposal problem.

A second technique in use is that of bacterial remediation of hydrocarbon spills. In these techniques, various specialized strains of bacteria have been developed which metabolize various hydrocarbons and gradually reduce them to carbon dioxide and water. Such remediation is the only process currently known which is capable of actually eliminating hydrocarbon contamination as opposed to merely absorbing it and removing it to a second location. However, such bacterial remediation requires that the bacteria and the hydrocarbon be brought into intimate contact under conditions in which the bacteria will act to metabolize the hydrocarbons. This requires extensive labor and effort to spread the bacteria on the soil and then to continually work and rework the contaminated area, turning and tilling the soil, until such time as the bacteria have been brought substantially into contact with all of the contaminated hydrocarbon particles. Further, this leaves a problem in that the bacteria may themselves be an undesirable or toxic contaminant in the soil, since the bacteria have been specially bred for the purposes of metabolizing and reducing hydrocarbons. Such bacteria may otherwise be an undesirable species for future use of the soil as a growing or plant support medium.

SUMMARY OF THE INVENTION

This invention pertains to materials for absorption of and decomposition of polluting hydrocarbons, especially waste oils and the like.

I have discovered that powdered cellulose when treated to form a suitable proportion of ammonium sulfate, creates a biologically active media which preferentially absorbs hydrocarbons in the presence of water, and which supports the growth of naturally occurring, hydrocarbon reducing bacterial forms, resulting in the rapid decomposition of absorbed hydrocarbons into water, carbon dioxide and benign waste products.

A suitable form of such cellulose material is obtained as a by-product of de-linting cotton seed. Prior art de-linting processes treat the cotton seed with sulfuric acid forming, as a by-product, a sulfuric acid-containing cellulosic material comprising approximately 95% cellulose (the removed cotton lint) and approximately 5% sulfuric acid. I have discovered that further treating the by-product material with ammonia forms a cellulose powder containing 5% (more or less) ammonium sulfate.

The resulting material is benign to handle, is in the form of a fine powder, and possesses significant adsorption properties in the presence of hydrocarbon oils. Specifically the material when fully wet with water will preferentially absorb oil or other hydrocarbons, expelling water to take up the oil or hydrocarbons. Further, the material supports rapid biological growth of existing bacteria, forming a rapid reaction bacterially remediated compound which results in the rapid decomposition of hydrocarbons by bacterial action.

It is, thus, an object of the invention to disclose a material which is particularly suited for remediating hydrocarbons.

It is a further object of the invention to disclose a material which rapidly adsorbs hydrocarbons or oil spills.

It is a further object of the invention to disclose a material which is capable of supporting bacteriological decomposition of hydrocarbons.

It is a further object of the invention to disclose a material and a method for the rapid decomposition of and removal of oil contamination from soils and the like.

It is a further object of the invention to disclose a material which can biologically remediate an oil spill in situ.

These and other objects of the invention are more clearly disclosed in the detailed description of the preferred embodiment which follows.

DETAILED DESCRIPTION OF THE INVENTION

The product and process of the invention are derived from a product developed in the treatment of the residue from a process for de-linting cotton seed with sulfuric acid. This process, used to clean cotton seed, results in a residue, the removed and altered lint or cotton fibers from the cotton seed, which are mixed with sulfuric acid. This solid waste material is about 92–97%, preferably 95%, cellulose and approximately 3–8% sulfuric acid residue.

This material was then treated with ammonia, producing a material comprising a 92–97%, preferably 95%, cellulose and 3–8% ammonium sulfate. In the course of testing this resulting material, it was discovered that the material had significantly enhanced hydrocarbon adsorption characteristics in comparison with calcined clay, the typical prior art oil absorbent. The absorption characteristics proved to be quite phenomenal as it was six times more effective than calcined clay on lighter liquids and up to ten times as effective with heavier viscosity hydrocarbons. Another apparent characteristic of the product is its ability to adsorb rather then absorb. This adsorption characteristic coupled with a tremendous wicking action, retains hydrocarbon products, and essentially eliminates leaching of the hydrocarbons into the surrounding environment, as demonstrated by various paint filter tests and by various tests in water filtration. The product was quite outstanding for retaining the hydrocarbons, but the most phenomenal characteristic was a unique tendency that, even though wet with water, when the product is brought in contact with hydrocarbons, it actually gives up the water and absorbs the hydrocarbon. This is a characteristic unknown in another product.

The absorbent/remediation product of the invention preferably possesses a ratio of total surface area of a particle to particle fineness (size) of greater than 1.0 and, preferably, greater than 1.5. A ratio greater than 1.0 is a result of the particle having a more exposed surface area due to etching out or fractionation of the cellulose particle. Such etching out or fractionation can be as a result of subjecting the particle to acidification, oxidation or other process which eats out or away a portion of the exposed surface area.

More particularly, this characteristic can be achieved through several process techniques including acidification with a strong acid such as sulfuric acid, nitric acid, phosphoric acid, hydrochloric acid, or the like; or oxidation through the use of oxidizing gases such as ozone, oxygen, $N_2O_3$, and the like.

A preferred product is one that has a total surface area of a particle to particle fineness (size) ratio of greater than 1.5 which was achieved using a process that does not destroy the microbes (bacteria, fungi, etc.) that are present in the cellulosic material media and which provides a properly balanced nutrient package (i.e., nitrogen, phosphorus, sulphur, oxygen, etc.) as an integral part of the process.

The resulting product provides an effective absorbent media for microbial proliferation when hydrated in the presence of a food source such as hydrocarbon contaminants.

The product can be stored and transported as a dry powder that surpasses other previously known compositions for degrading hydrocarbons and other related carbon-based contaminants in speed, efficiency, shelf life, ease of application, VOC control (vapor suppression), ground water contamination control and control of such additives as phosphates and nitrates normally associated with degradation of hydrocarbons.

Total surface area is normally measured by an ASTM gas adsorption procedure, such as typical of ASTM-D-4820 amended to test the particles under consideration.

Total particle fineness can be calculated using a conventional screen analysis evaluation, or electron microscope according to a procedure, such as for example set forth in ASTM-D-3844-5.

An experiment was designed to study the characteristic of absorption and total encapsulation of hydrocarbon and to determine just how effective it would be compared to other absorbents. In this experiment equal amounts of diesel fuel were mixed with each of four absorbents. The four absorbents selected were (1) peat moss, (2) a cellulosic-type product called Fiber Pearl, (3) one called Cell-U-Sorb and (4) the fibrous product of the invention. Each of these diesel fuel absorbent mixtures was mixed with equal volumes of potting soil and then separated into two parts.

In one part, a flower was planted, with all plants being watered normally. It was expected that in a short period of time all the plants would die. Within ten (10) days three (3) of the plants were dead but the plant in the product of invention shed two to three leaves from the bottom portion of the plant and continued to bloom. This was observed for a total of sixty (60) days. The plant continued to live but did not put on new growth.

In about eighty (80) days, the plant in the product of the invention started to sprout new growth. This phenomena raised a working hypothesis that there was microbial action or bioremediation in the soil, apparently contributed by microorganisms indigenous to the inventive adsorbent itself. The invention adsorbent is a cellulose derived from an oil bearing plant (cotton seeds). Cellulose from peanut hulls, rice hulls, corn cobs, soybeans or other oil-bearing plants is believed to have similar microbial and physical characteristics.

In a second test, a new plant was planted in the remaining samples of the diesel fuel contaminated material without additional moisture. The other three (3) plants died and the product of invention kept the plant alive but without growth. It was completely unexpected that one part of the contaminated dirt now grew a flower, and one part, even though sitting in the same room, did not support growth. As the only difference between the soils was the first set of material with the growing flower was kept damp during the time of the experiment. It appears that the moisture and oxygen to the soil enhanced the growth of indigenous bacteria, thus causing bioremediation of the soil. Soil without moisture did not start bacterial digestion of the hydrocarbon and remained dormant.

Several other experiments have attempted to measure or gauge the encapsulating characteristics of this product and the remediation tendencies of this product. A very simple experiment was done to adsorb a hydrocarbon in the product, not to saturation, but to a point where the product remained dry to the touch; this product was then placed in a dish and kept damp in a relatively warm climate. It was noticed that within three (3) to four (4) days the material would be covered with a moss or fungus growth. This is considered to indicate that some bacterial action was taking place, either mold bacteria or some indigenous material in the product.

The next experiments with this product attempted to determine its ability to remediate soil or to remediate hydrocarbons. Historically, remediation chemicals and biological processes for the reduction of spilled hydrocarbons and crude oil spills have depended upon the development of special strains of bacteria which must be brought into contact with the hydrocarbons in order to react to the hydrocarbons and reduce them to more benign materials. Such bacterial strains are expensive and lengthy in time to develop, and the use of the bacteria is labor intensive. It is necessary to break the oil droplets as small as possible so that they can be brought into contact with bacteria. This usually requires the addition of an emulsion agent and the bacteria to the contaminated soil, and this results in an extensive and repeated process of milling the soil, mixing the soil with the bacteria and emulsion agent, aerating the resulting mixture for oxygen, (a necessary component for all bacterial remediation of hydrocarbons) and then repeated tilling until the bacteria has been brought in contact with substantially all the emulsified oil.

The inventive product here described, because of its unusual hydrocarbon absorption characteristics and the fact that it is physically a dust, has a natural encapsulation characteristic to draw hydrocarbons out of the soil. By its strong wicking action, it holds the particles of hydrocarbon in each particle of the product, drawing the particles in contact with the naturally occurring bacteria within the product. It appears that the presence of the ammonium sulfate together with trace phosphorus (phosphate) inherent in cotton lint, acts as a nutrient for the bacteria so that with the addition of suitable amounts of moisture and oxygen contact, the bacterial activity is naturally enhanced, causing a significant increase in the speed with which hydrocarbons are bacterially removed from the soil.

An unexpected property of the product is that it stabilizes the soil, because its strong wicking action eliminates much of the labor required for prior art bacterial remediation of hydrocarbon contaminated soils. So long as the pH of the product is between 3 to 9, preferably between 4.5 to 9, it can simply be spread upon the contaminated ground and tilled or disked in using standard farm equipment. The product draws the hydrocarbon preferentially to itself, and, once the soil is moistened, the product, containing its own nutrients, starts and enhances bacterial growth.

In one experiment, soils with high levels of hydrocarbons were covered with the product of the invention, tilled until they became sludge-like, and left standing for a period of sixty days. Within the sixty day period, the original level of hydrocarbon, approximately 70,000 ppm in the sludge, had been reduced by 95%.

In another test, a hydrocarbon sludge pit consisting of contaminated soil showing hydrocarbon levels between 60,000 and 90,000 ppm was treated by spreading the product of the invention throughout the pit area and tilling it into the soil. Areas having greater hydrocarbon content were noticeably darker; these areas were treated with higher levels of the product until the treated soil was of a uniform consistent coloration. The site was observed and kept damp for a period of sixty days. At the end of the sixty day period, new grass had begun to grow on soil which previously had been barren and black in color.

In both tests, no additional aeration or tilling was required once the product had been tilled into the soil.

This product, comprising a powdery cellulose material with approximately 3–8% effective nitrogen bearing nutrient and trace phosphorus, supports the enhanced growth of indigenous microorganisms which are encapsulated in the cellulosic adsorbent. The cellulose is derived from oil-bearing plants (i.e. cotton seed) and is believed to have indigenous microorganisms that adapt readily to metabolize oils. The cellulose, when moistened, adsorbs and binds hydrocarbons; the nutrients rapidly develop large indignous bacterial populations which are active in the reduction of the adsorbed hydrocarbons to benign by-products, particularly water and carbon dioxide. In addition, the treated powdered cellulosic material has a particularly high absorption of hydrocarbons and, therefore, enhances the movement of the hydrocarbons from the soil into contact with the enhanced bacterial populations. The end result is a material which has a significantly greater effectiveness in the reduction of hydrocarbons within the soil and a significantly enhanced speed of reduction with minimum labor.

An alternate treatment of cottonseed treats the seed with hydrochloric acid to separate the lint. While the chloride tends to act as a bactericide, treatment of the acid-treated lint with ammonium sulfate or ammonium phosphate apparently stops the bactericide action, preserving the desirable microorganisms and leaving the desired nutrient residue so that cotton lint so treated is also effective in the process.

Tests of the cellulose material of the invention indicate that one part of phosphorus to ten parts of sulfur as sulfate to one hundred parts of nitrogen as nitrate should be present for optimum nutrient content. Since most distilled hydrocarbons and oils contain both sulfur and phosphorus, it is usually sufficient that the cellulose contain only the nitrate, although some sulfate and phosphate will generally be found in the treated cellulose.

The effective adsorbent resulting from this product and process acts as a physical emulsification agent, encapsulating the contaminants and holding them in close contact with microorganisms which rapidly metabolize the hydrocarbon as an additional food source.

The patent extends, therefore, both to the process for remediating hydrocarbon contaminated soils, as well as to the product used for the remediation, all set forth in the claims.

It is claimed:

1. A method of treating hydrocarbon contaminated soils to remove a hydrocarbon comprising (a) providing a composition comprising a cellulose derived from an oil-bearing plant including therein bacteria which is a naturally present component of the cellulose and naturally occurs in said cellulose and at least one nutrient, and said composition being characterized by having ability to absorb water and hydrocarbon material as well as release water absorbed by said composition in favor of absorbing additional hydrocarbon material but which will not release hydrocarbon material previously absorbed by said composition; (b) applying said composition of (a) into hydrocarbon contaminated soil by tilling or disking; (c) wetting the soil subsequent to application (b) to establish and maintain a continuous moist condition in said soil; and (d) leaving said soil in said continuous moist condition for a period of time, whereby said method provides absorption of hydrocarbon material from said soil by said composition.

2. A method of treating hydrocarbon contaminated soils to remove a hydrocarbon comprising (a) providing a composition comprising a cellulose derived from an oil-bearing plant including therein bacteria which is a naturally present component of the cellulose and naturally occurs in said cellulose, wherein said cellulose is treated with an acid to acidify said cellulose and provide at least one nutrient to said cellulose, and, thereafter, said cellulose is neutralized by treating said cellulose with ammonia to a pH of between 3–9 in a manner so as not to kill said bacteria present in said cellulose, and said composition being characterized by having ability to absorb water and hydrocarbon material as well as release water absorbed by said composition in favor of absorbing additional hydrocarbon material but which will not release hydrocarbon material previously absorbed by said composition; (b) applying said composition of (a) into hydrocarbon contaminated soil by tilling or disking; (c) wetting the soil subsequent to application (b) to establish and maintain a continuous moist condition in said soil; and (d) leaving said soil in said continuous moist condition for a period of time, whereby said method provides absorption of hydrocarbon material from said soil by said composition.

3. A method according to claim 1 or claim 2 wherein said period of time is a period of at least 60 days.

4. A method according to claim 1 or claim 2 wherein said oil-bearing plant is selected from a group consisting of cotton seeds, cotton lint, peanut hulls, rice hulls, corncobs and soy beans.

5. A method according to claim 1 or claim 2 wherein said cellulose is in a powder form.

6. A method according to claim 1 or claim 2 wherein said at least one nutrient is selected from a group consisting of nitrogen, sulfur and phosphorus.

7. A method according to claim 2 wherein said acid is present in an amount of from 3–8%.

8. A method according to claim 2 wherein said acid is sulfuric acid and said composition provided includes 92–97% cellulose and 3–8% ammonium sulfate.

9. A method according to claim 1 or claim 2 wherein said composition is in particulate form and each particle has a total surface area to particle fineness ratio of greater than 1.0.

10. A composition for treating by adsorption and remediation hydrocarbon contaminated soils which absorbs water and hydrocarbon material from said soil and following absorption of water, said composition will release water absorbed in favor of absorbing additional hydrocarbon material but which will not release hydrocarbon material previously absorbed, wherein said composition comprises a cellulose derived from an oil-bearing plant including therein (1) bacteria which is a naturally present component of the cellulose and naturally occurs in said cellulose and (2) at least one nutrient.

11. A composition for treating by adsorption and remediation hydrocarbon contaminated soil which absorbs water and hydrocarbon material from said soil and following absorption of water, said composition will release water absorbed in favor of absorbing additional hydrocarbon material but which will not release hydrocarbon material previously absorbed, wherein said composition comprises a cellulose derived from an oil-bearing plant including therein bacteria which is a naturally present component of the cellulose and naturally occurs in said cellulose, wherein said cellulose is treated with an acid to acidify said cellulose and provide at least one nutrient to said cellulose and, thereafter, said cellulose is neutralized by treating said cellulose with ammonia to a pH of between 3–9 in a manner so as not to kill said bacteria in said cellulose.

12. A composition according to claim 10 or claim 11 wherein said oil-bearing plant is selected from a group consisting of cotton seeds, cotton lint, peanut hulls, rice hulls, corncobs and soy beans.

13. A composition according to claim 10 or claim 11 wherein said cellulose is in powder form.

14. A composition according to claim 10 or claim 11 wherein said at least one nutrient is selected from a group consisting of nitrogen, sulfur and phosphorus.

15. A composition according to claim 11 wherein said acid is present in an amount of from 3–8%.

16. A composition according to claim 11 wherein said acid is sulfuric acid and said composition provided includes 92–97% cellulose and 3–8% ammonium sulfate.

17. A composition according to claim 13 wherein a particle of the powder has a total surface area to particle fineness ratio of greater than 1.0.

18. An adsorbent remediation cellulosic product prepared by a process comprising (1) treating (a) a cellulose derived from an oil-bearing plant including therein bacteria which is a naturally present component of the cellulose and naturally occurs in said cellulose with (b) an acid to provide (c) an acidified cellulosic material containing said bacteria and at least one nutrient; and (2) treating the acidified cellulosic material (c) with ammonia to a pH of from 3–9 in a manner so as not to kill the bacteria present in said cellulosic material; wherein said product is characterized by having ability to absorb water and hydrocarbon material as well as release water absorbed by said product in favor of absorbing additional hydrocarbon material, and is not subject to leaching of said hydrocarbon material from said product.

19. A product according to claim 18 wherein said acid is selected from a group consisting of sulfuric acid, phosphoric acid, hydrochloric acid, and nitric acid.

20. A product according to claim 18 wherein said acid is hydrochloric acid, and ammonium phosphate or ammonium sulfate are used in place of said ammonia.

21. A product according to claim 18 wherein said acid is sulfuric acid and a sulfuric acid-containing cellulosic material is produced which when treated with said ammonia provides an ammonium sulfate-containing cellulosic material.

22. A product according to claim 21 wherein said sulfuric acid-containing cellulosic material is 92–97% cellulose and 3–8% sulfuric acid residue.

23. A product according to claim 21 wherein said ammonium sulfate-containing cellulosic material is 92–97% cellulose and 3–8% ammonium sulfate.

24. A product according to claim 18 wherein said oil-bearing plant is selected from a group consisting of cotton seeds, cotton lint, peanut hulls, rice hulls, corncobs, and soybeans.

25. A product according to claim 18 wherein said cellulose is in powder form.

26. A product according to claim 25 wherein a particle of the powder has a total surface area to particle fineness ratio of greater than 1.0.

27. A product according to claim 18 wherein said at least one nutrient is selected from a group consisting of nitrogen, sulfur and phosphorus.

28. A product according to claim 18 wherein said acid is present in an amount of from 3–8%.

29. An adsorbent remediation cellulosic product prepared by a process comprising oxidating a cellulose derived from an oil-bearing plant including therein bacteria which is a naturally present component of the cellulose and naturally occurs in said cellulose to fractionate said cellulose; wherein said product is characterized by having ability to absorb water and hydrocarbon material as well as release water absorbed by said product in favor of absorbing additional hydrocarbon material, and is not subject to leaching of said hydrocarbon material from said product.

30. A product according to claim 29 wherein said oil-bearing plant is selected from a group consisting of cotton seeds, cotton lint, peanut hulls, rice hulls, corncobs, and soybeans.

31. A product according to claim 29 wherein said cellulose is in powder form.

32. A product according to claim 31 wherein a particle of the powder has a total surface area to particle fineness ratio of greater than 1.0.

33. A product according to claim 29 wherein said oxidation is carried out using an oxidizing gas.

* * * * *